United States Patent
Zeng et al.

(10) Patent No.: US 9,936,654 B2
(45) Date of Patent: Apr. 10, 2018

(54) ***DENDROBIUM* IN VITRO CROSSBREEDING METHOD**

(71) Applicant: SOUTH CHINA BOTANICAL GARDEN, CHINESE ACADEMY OF SCIENCES, Guangzhou, Guangdong (CN)

(72) Inventors: Songjun Zeng, Guangdong (CN); Kunlin Wu, Guangdong (CN); Jianxia Zhang, Guangdong (CN); Feng Zheng, Guangdong (CN); Jun Duan, Guangdong (CN)

(73) Assignee: SOUTH CHINA BOTANICAL GARDEN, CHINESE ACADEMY OF SCIENCES, Guangdong (CN)

( * ) Notice: Subject to any disclaimer, the term of this patent is extended or adjusted under 35 U.S.C. 154(b) by 148 days.

(21) Appl. No.: 14/903,476

(22) PCT Filed: Jul. 19, 2013

(86) PCT No.: PCT/CN2013/079683
§ 371 (c)(1),
(2) Date: Jan. 7, 2016

(87) PCT Pub. No.: WO2015/003408
PCT Pub. Date: Jan. 15, 2015

(65) Prior Publication Data
US 2016/0143236 A1 May 26, 2016

(30) Foreign Application Priority Data
Jul. 8, 2013 (CN) .......................... 2013 1 0285055

(51) Int. Cl.
*A01H 1/02* (2006.01)
*A01H 4/00* (2006.01)

(52) U.S. Cl.
CPC ................. *A01H 1/02* (2013.01); *A01H 4/00* (2013.01); *A01H 4/005* (2013.01)

(58) Field of Classification Search
None
See application file for complete search history.

(56) References Cited

U.S. PATENT DOCUMENTS

2009/0176227 A1* 7/2009 Chen ........................ A01H 1/08
435/6.13

FOREIGN PATENT DOCUMENTS

| CN | 1631107 A | 6/2005 |
|---|---|---|
| CN | 101461328 A | 6/2009 |
| CN | 101569287 A | 11/2009 |
| CN | 102239801 A | 11/2011 |
| CN | 102283114 A | 12/2011 |
| CN | 102283120 A | 12/2011 |
| CN | 102630568 A | 8/2012 |

OTHER PUBLICATIONS

Zhang, 2011 Fujian Agriculture Science and Technology 6: 88-90, w/English abstract.*
Zhang, "Rapid propagating techniques of artificial cross breeding of Dendrobium candidum", Longyan Institute of Agricultural Sciences, Fujian Agriculture Science and Technology, vol. 6, pp. 88-90, China, 2011, w/English abstract (3 pages).
International Search Report dated Apr. 25, 2014, issued in counterpart Application No. PCT/CN2013/079683 (2 pages).

\* cited by examiner

*Primary Examiner* — Amjad Abraham
*Assistant Examiner* — Bratislav Stankovic
(74) *Attorney, Agent, or Firm* — Westerman, Hattori, Daniels & Adrian, LLP

(57) ABSTRACT

The invention discloses a *Dendrobium* in vitro crossbreeding method. The method can be used to greatly shorten the maturation period of fruits, to enable a hybrid to bloom in vitro in a short period so as to observe flower shapes and colors, and to cultivate a novel variety, thus accelerating *Dendrobium* breeding, the first such report internationally. Since in vitro *Dendrobium* blooms annually, it enables crossbreeding of varieties having different inflorescences in nature. In addition, the medium used at each stage of the invention utilizes Hyponex which has a unique composition and costs little, thus allowing for a high blossoming rate and rapid fruit development. Also, only simple plant tissue culture equipment is required for implementing the invention, thus the entire breeding method is simple and low cost, and provides conditions for cultivating of high-quality *Dendrobium* varieties.

4 Claims, No Drawings

DENDROBIUM IN VITRO CROSSBREEDING METHOD

FIELD OF THE INVENTION

This invention relates to the field of plant breeding, in particular to a *Dendrobium* in vitro crossbreeding method.

BACKGROUND OF THE INVENTION

There are about 1600 species in the *Dendrobium* genus (Orchidaceae), with more than 70 species found in China. Most *Dendrobium* species have high ornamental value, and *Dendrobium* is one of the most important genera of the global orchid industry. Most ornamental *Dendrobium* species on the market are cross breeds. The Conventional *Dendrobium* crossbreeding cycle is very long and generally takes 4-6 years to cultivate a new crossbreeding variety. In addition, it is often difficult to perform hybridization between some species with different inflorescences. Even when pollen is stored at low temperature, hybridization is often prone to failure due to pollen contamination or pollen inactivation.

SUMMARY OF THE INVENTION

The objective of this invention is to provide a method of crossbreeding *Dendrobium* in vitro to establish novel varieties and shorten the breeding period.

The *Dendrobium* in vitro crossbreeding method includes the following steps:

Materials: artificial pollination is conducted on selected healthy actively growing *Dendrobium* stock plants of different varieties during the flowering period. After fruits have matured, seeds contained in the fruits are aseptically sown;

a. aseptic sowing: after sterilization, the fruits are first rinsed several times with sterilized water then cut open. The yellowish-white powder-like embryo contained in the fruits is inoculated onto seed germination medium with an inoculating needle and developed under the following culture conditions: temperature of 24-28° C., illuminance of 1500-2000 1×, and an illumination period of 12-16 hours per day. These conditions allow the seed to geminate and form a protocorm that will grow until a complete plantlet with a height of 2-3 centimeters is formed;

b. in vitro flowering induction and in vitro crossbreeding: the complete plantlet with a height of 2-3 centimeters is transferred onto in vitro flowering induction medium and cultured under the following conditions: temperature of 24-28° C., illuminance of 1500-2000 1×, and an illumination period of 12-16 hours per day until the plantlet blooms. Under aseptic conditions, interspecific pollination is performed artificially between selected in vitro *Dendrobium* flowers of different varieties having normal flower colors and shapes. After pollination, flowering plants are transferred to rooting and growth-promoting medium and cultured under the following culture conditions: temperature of 24-28° C., illuminance of 1500-2000 1×, and an illumination period of 12-16 hours per day, until the fruits have matured;

c. combination of aseptic sowing and in vitro flowering induction of hybrids: the fruit of step b matured in vivo is cut open, and a embryo contained in the fruit is sown onto seed germination medium and cultured under the following culture conditions: temperature of 24-28° C., illuminance of 1500-2000 1×, and an illumination period of 12-15 hours per day. These conditions allow the seed to germinate and form a protocorm that will grow until a complete plantlet is formed, and then the plantlet is transferred onto in vitro flowering induction medium and cultured under the following culture conditions: temperature of 24-28° C., illuminance of 1500-2000 1×, and an illumination period of 12-16 hours per day, for flowering induction. This allows the flower shapes and colors of the hybridized combination to be observed after the in vitro plantlet blooms;

d. tissue culture of new varieties: after the plantlet blooms, tissue culture is conducted on selected lines having excellent flower shapes and colors. In this step, a stem apex or stem node of a selected line used as an explant is cultured on a protocorm induction and subculture/proliferation medium to induce protocorms and for subculture to proliferation them. This takes place under the following culture conditions: temperature of 24-28° C., illuminance of 1500-2000 1×, and an illumination period of 12-15 hours per day, for subculture/proliferation, allowing protocorm-like bodies (PLB) to form. The PLBs are transferred onto rooting and growth-promoting medium and cultured under the following conditions: temperature of 24-28° C., illuminance of 1500-2000 1×. and an illumination period of 12-16 hours per day, for rooting and promoting growth, so as to obtain in vitro plantlets:

e. transplanting of in vitro plantlets: when the in vitro plantlets have grown to 3-4 centimeters in height, they are transplanted for hardening under natural light. Hardened plantlets are then transplanted onto a substrate and cultured to obtain *Dendrobium* hybrid seedlings;

the seed germination medium contains the following components per liter: 2-3 grams of HYPONEX® No. 1, 0.5-2 grams of peptone, 50-100 milliliters of coconut milk, 15-30 grams of sucrose, vitamin elements (including myo-inositol) the same as those in MS medium, 0.5-1 grams of activated carbon, a conventional amount of agar, and the balance of water, at pH 5.2-5.4;

the in vitro flowering induction medium contains the following components per liter: 1-1.5 grams of HYPONEX® No. 1, 1-1.5 grams of HYPONEX® No. 2, 0.1-0.3 grams of casein hydrolysate, 0.5-3.0 milligrams of 6-benzyladenine (BA), 0.1-0.5 milligrams of naphthylacetic acid (NAA), 0.1-0.5 milligrams of paclobutrazol, 30-40 grams of sucrose, vitamin elements (including myo-inositol) the same as those in MS medium, a conventional amount of agar, and the balance of water, at pH 5.2-5.4;

the rooting and growth-promoting medium contains the following components per liter: 1-2 grams of HYPONEX® No. 1, 1-1.5 grams of HYPONEX® No. 2, 0.5-2 grams of peptone, 15-30 grams of sucrose, vitamin elements (including myo-inositol) the same as those in MS medium, 0.1-0.5 milligrams of NAA, 50-100 grams of banana juice, 0.5-1 gram of activated carbon, a conventional amount of agar, and the balance of water, at pH 5.2-5.4; and the protocorm induction and subculture/proliferation medium contains the following components per liter: 1-2 grams of HYPONEX® No. 1, 1-1.5 grams of HYPONEX® No. 2, 0.5-2 grams of peptone, 50-100 milliliters of coconut milk, 20-30 grams of sucrose, vitamin elements (including myo-inositol) the same as those in MS medium, 0.5-2.0 milligrams of BA, a conventional amount of agar, and the balance of water, at pH 5.2-5.4.

For the aseptic sowing step a, the fruit sterilizing step and then the rinse of fruit with sterilized water several times preferably includes, at first, soaking the fruit in 75% ethanol (volume/volume) for 30 seconds, then sterilizing the fruit in 0.1% mercuric chloride solution (weight/weight) for 20 minutes, and rinsing the fruit with sterilized water 4-5 times.

The PLBs of step d may also be re-inoculated to new protocorm induction and subculture/proliferation medium under the following conditions: culture temperature of 24-28° C., illuminance of 1500-2000 1×. and an illumination period of 12-16 hours per day, for subculture/proliferation, to form PLBs. PLBs are then transferred onto rooting and growth-promoting medium, for rooting and promoting growth.

The transplanting of in vitro plantlets is preferably conducted when the in vitro plantlets have grown to a height of 3-4 centimeters and with 2-3 shoot in each chimp. The in vitro plantlets are transplanted to harden them under natural light for 10 days. They are then removed from glass vessels, separating agarized medium from roots by washing: and then the cultivating hardened plantlets in a mixed substrate containing peat and Lan Stones (special stones that produced in China for orchid cultivation) at a 1:1 volumetric ratio. Plantlets are cultured under natural conditions to obtain *Dendrobium* hybrid seedlings. This process will result in transplant survival greater than 95%.

The HYPONEX® No. 1 and HYPONEX® No. 2 are products of the prior art (from Taihe Horticultural Co. Ltd. (Taiwan)), and can be purchased commercially HYPONEX® No. 1 is a fertilizer containing 7 wt % of total nitrogen (including 1.2% of ammonium nitrogen and 5.8% of nitrate nitrogen), 6 wt % of water-soluble phosphoric anhydride and 19 wt % of water-soluble potassium oxide. HYPONEX® No. 2 is a fertilizer containing 20 wt % of total nitrogen (including 4% of ammonium nitrogen and 4% of nitrate nitrogen), 20 wt % of water-soluble phosphoric anhydride and 20 wt % of water-soluble potassium oxide.

In the seed germination medium, the vitamin elements (including myo-inositol) the same as those in MS medium refer to the content of vitamin elements (including myo-inositol) per liter of the seed germination medium is equal to the content of vitamin elements (including myo-inositol) per liter in the MS medium. The terms in vitro flowering induction medium, rooting and growth-promoting medium, and protocorm induction and subculture/proliferation medium should be interpreted as they are written.

The main intended use of agar is to solidify the medium, and the amount of the agar in a medium is conventional knowledge in the art, generally being 6-8%.

The in vitro crossbreeding method of this invention can be used to shorten the maturation period of fruits, to enable a hybrid to bloom in vitro in a short period so as to observe flower shapes and colors, and to cultivate a novel variety, thus accelerating *Dendrobium* breeding. This is the first report internationally. Since in vitro *Dendrobium* blooms annually, it enables crossbreeding of varieties having different inflorescences in nature. In addition, the medium used at each stage of the invention utilizes "HYPONEX®" as the main fertilizer, which has a unique composition and low cost, allowing a high blossoming rate and rapid fruit development. In addition, only simple and standard plant tissue culture devices, equipment and tools are required to implement the invention, thus the entire breeding method is simple and economical, and provides conditions for cultivating *Dendrobium* varieties with high quality.

DETAILED DESCRIPTION OF THE EMBODIMENTS

The following embodiments further illustrate the invention, but do not limit the invent ion.

Embodiment 1: Crossbreeding of *Dendrobium officinale* and *Dendrobium huoshanense*

1. Materials: intraspecific cross pollination is artificially conducted respectively on selected healthy actively growing stock plants of *D. officinale* and *D. huoshanense* (*D.* is the abbreviation for *Dendrobium*) during the flowering period. 110 days after pollination, when the fruits of the two *Dendrobium* varieties have substantially matured, the seeds contained in respective fruits are aseptically sown.

2. Aseptic sowing: during sowing, the fruits are first soaked in 75% ethanol for 30 seconds, then sterilized in 0.1% mercuric chloride solution for 20 minutes, and rinsed 4 times with sterilized water; and then the fruits are cut open, and the yellowish-white powder-like embryo contained in the fruits is inoculated onto seed germination medium with an inoculating needle and developed under the following culture conditions: temperature of 24-28° C., illuminance of 1500-2000 1×, and an illumination period of 12 hours per day. The seed begins to germinate in about 12 days and thus forms a protocorm, and a complete plantlet with a height of 2-3 centimeters is formed in 75 days.

3. In vitro flowering induction and in vitro crossbreeding: the complete plantlets of *D. officinale* and *D. huoshanense* with a height of 2-3 centimeters are transferred onto in vitro flowering induction medium and cultured for about 50 days under the following conditions: temperature of 24-28° C., illuminance of 1500-2000 1×, and an illumination period of 12 hours per day, with the flowering rate of *D. officinale* being 50% and the flowering rate of *D. huoshanense* being 30%. Interspecific pollination is performed artificially on a super-clean bench between selected in vitro *Dendrobium* flowers of different varieties having normal flower colors and shapes. After pollination, the flowering plants are transferred onto a rooting and growth-promoting medium and cultured under the following culture conditions: temperature of 24-28° C., illuminance of 1500-2000 1×, and an illumination period of 12 hours per day. The fruits are matured in just 50 days.

4. Combination of aseptic sowing and in vitro flowering induction of hybrids: the fruit of the previous step matured in vivo is harvested and then cut open without sterilization. The embryo contained in the fruit is sown onto seed germination medium and cultured under the following culture conditions: temperature of 24-28° C., illuminance of 1500-2000 1×, and an illumination period of 12 hours per day. The seed of the hybridized combination germinates to form a protocorm in about 10 days, and a complete plantlet is formed in 60 days. Then the plantlet is transferred onto in vitro flowering induction medium and cultured under the following culture conditions: temperature of 24-28° C., illuminance of 1500-2000 1×, and an illumination period of 12 hours per day, for flowering induction. This allows the flower shapes and colors of the hybridized combination to be observed after the in vivo plantlet blooms.

5. Tissue culture of new varieties: since both of the crossing parents are native species, the flower shapes and colors of the hybrid progenies are not varied. The stem apex or stem node of a healthily-growing and flowering line selected as the explant is cultured on protocorm induction and subculture/proliferation medium under the following culture conditions: temperature of 24-28° C., illuminance of 1500-2000 1×, and an illumination period of 12 hours per day, for subculture/proliferation. After 30 days, the proliferation times can be 5 (which means the amount is 5 times as the original), and the formed protocorm-like body (PLB) can further proliferate. The PLB may also be transferred onto rooting and growth-promoting medium under the following culture conditions: temperature of 24-28° C., illuminance of 1500-2000 1×, and an illumination period of 12 hours per day, for rooting and promoting growth, so as to obtain in vitro plantlets.

6. Transplanting of in vitro plantlets: The transplanting of in vitro plantlets is conducted when the in vitro plantlets have grown to 3-4 centimeters in height and having 2-3 shoots in each clump. The in vitro plantlets are transplanted to harden them under natural light for 10 days; they are then removed from glass vessels, separating agarized medium from roots by washing, and then the cultivating hardened plantlets in a mixed substrate containing peat and special stones for orchid cultivation (at a 1:1 volumetric ratio), and cultured under conditions that proper ventilation and sufficient moisture are maintained (normal conditions), so as to obtain *Dendrobium* hybrid seedlings, with the transplant survival rate greater than 95%.

The seed germination medium contains the following components per liter: 2 grams of HYPONEX® No. 1, 0.5 grams of peptone, 50 milliliters of coconut milk, 15 grams of sucrose, vitamin elements (including myo-inositol) the same as those in MS medium, 0.5 grams of activated carbon, 6.5 grams of agar, and the balance of water, at pH 5.2-5.4. The aforementioned components are mixed uniformly and then subject to high temperature sterilization for later use.

The in vitro flowering induction medium contains the following components per liter: 1 gram of HYPONEX® No. 1, 1 gram of HYPONEX® No. 2, 0.1 grams of casein hydrolysate, 0.5 milligrams of 6-benzyladenine (BA), 0.1 milligrams of naphthylacetic acid (NAA), 0.1 milligrams of paclobutrazol, 30 grams of sucrose, vitamin elements (including myo-inositol) the same as those in MS medium, 6.5 grams of agar, and the balance of water, at pH 5.2-5.4. The aforementioned components are mixed uniformly and then are subject to high temperature sterilization for later use.

The rooting and growth-promoting medium contains the following components per liter: 1 gram of HYPONEX® No. 1, 1 gram of HYPONEX® No. 2, 0.5 grams of peptone, 15 grams of sucrose, vitamin elements (including myo-inositol) the same as those in MS medium, 0.1 milligrams of NAA, 50 grams of banana juice, 0.5 grams of activated carbon, 6.5 grams of agar, and the balance of water, at pH 5.2-5.4. The aforementioned components are mixed uniformly and then are subject to high temperature sterilization for later use.

The protocorm induction and subculture/proliferation medium contains the following components per liter: 1 gram of HYPONEX® No. 1, 1 gram of HYPONEX® No. 2, 0.5 grams of peptone, 50 milliliters of coconut milk, 20 grams of sucrose, vitamin elements (including myo-inositol) the same as those in MS medium, 0.5 milligrams of BA, 6.5 grams of agar, and the balance of water, at pH 5.2-5.4. The aforementioned components are mixed uniformly and then subject to high temperature sterilization for later use.

The culture conditions in each of the aforementioned seed germination medium, the in vitro flowering induction medium, the rooting and growth-promoting medium, and the protocorm induction and subculture/proliferation medium are: temperature of 24-28° C., illuminance of 1500-2000 1×, and an illumination period of 12 hours per day.

Embodiment 2: Crossbreeding of *Dendrobium nobile* and *Dendrobium unicum*

1. Materials: pollination is artificially conducted on selected healthily-growing stock plants of *D. nubile* and *D. unicum* during the flowering period; 130 days after pollination, when the fruits of the two *Dendrobium* varieties have substantially matured, the seeds found in the respective fruits are aseptically sown.

2. Aseptic sowing: sowing, the fruits are frit soaked in 75% ethanol for 30 seconds, then sterilized in 0.1% mercuric chloride solution for 20 minutes, and rinsed 4 times with sterilized water; and then the fruits are cut open, and the yellowish-white powder-like embryo contained in the fruits is inoculated onto seed germination medium with an inoculating needle and developed under the following culture conditions: temperature of 24-28° C., illuminance of 1500-2000 1×, and an illumination period of 14 hours per day. The seed begins to germinate in about 12 days and thus limns a protocorm, and a complete plantlet is formed in 75 days.

3. In vitro flowering induction and in vitro crossbreeding: the complete plantlets with a height of 2-3 centimeters are transferred onto in vitro flowering induction medium and cultured under the following conditions: temperature of 24-28° C., illuminance of 1500-2000 1×, and an illumination period of 14 hours per day, with 50 days later the flowering rate of *D. nobile* being 40% and the flowering rate of *D. unicum* being 50%. Interspecific pollination is performed artificially on a super-clean bench between selected in vitro flowers of *D. nobile* and *D. unicum* having normal flower colors and shapes. After pollination, the flowering plants are transferred onto a rooting and growth-promoting medium and cultured. The fruits are matured in just 55 days.

4. Combination of aseptic sowing and in vitro flowering induction of hybrids: the fruit of the previous step matured in vivo is harvested and then cut open without sterilization. The embryo contained in the fruit is sown onto seed germination medium and cultured under the following culture conditions: temperature of 24-28° C., illuminance of 1500-2000 1×, and an illumination period of 14 hours per day. The seed of the hybridized combination germinates to form a protocol in about 10 days, and a complete plantlet is formed in 70 days. Then the plantlet is transferred onto in vitro flowering induction medium and cultured under the following culture conditions: temperature of 24-28° C., illuminance of 1500-2000 1×, and an illumination period of 14 hours per day, for flowering induction. This allows the flower shapes and colors of the hybridized combination to be observed after the in vivo plantlet blooms.

5. Tissue culture of new varieties: since both of the crossing parents are native species, the flower shapes and colors of the hybrid progenies are not varied. The stem apex or stem node of a healthily-growing and flowering line selected as the explant is cultured on protocorm induction and subculture/proliferation medium under the following culture conditions: temperature of 24-28° C., illuminance of 1500-2000 1×, and an illumination period of 14 hours per day, for subculture/proliferation. After 35 days, the proliferation times can be 4.5 (which means the amount is 4.5 times as the original), and the formed PLB can further proliferate. The PLB may also be transferred onto rooting and growth-promoting medium under the following culture conditions: temperature of 24-28° C., illuminance of 1500-2000 1×, and an illumination period of 14 hours per day, for rooting and promoting growth, so as to obtain in vitro plantlets.

6. Transplanting of in vitro plantlets: The transplanting of in vitro plantlets is conducted when the in vitro plantlets have grown to 3-4 centimeters in height and having 2-3 shoots in each clump. The in vitro plantlets are transplanted to harden them under natural light for 10 days; they are then removed from glass vessels, separating agarized medium from roots by washing, and then the cultivating hardened plantlets in a mixed substrate containing peat and special stones for orchid cultivation (at a 1:1 volumetric ratio), and cultured under conditions that proper ventilation and sufficient moisture are maintained (normal conditions), so as to obtain *Dendrobium* hybrid seedlings, with the transplant survival rate water than 90%.

The seed germination medium contains the following components per liter: 2.5 grams of HYPONEX® No. 1, 1 gram of peptone, 75 milliliters of coconut milk, 20 grams of sucrose, vitamin elements (including myo-inositol) the same as those in MS medium, 0.75 grams of activated carbon, 6.5 grams of agar, and the balance of water, at pH 5.2-5.4. The aforementioned components are mixed uniformly and then subject to high temperature sterilization for later use.

The in vitro flowering induction medium contains the following components per liter: 1.2 grams of HYPONEX® No. 1, 1.2 grams of HYPONEX® No. 2, 0.2 grams of casein hydrolysate, 1.0 milligrams of 6-benzyladenine (BA), 0.3 milligrams of naphthylacetic acid (NAA), 0.3 milligrams of paclobutrazol, 35 grams of sucrose, vitamin elements (including myo-inositol) the same as those in MS medium, 6.5 grams of agar, and the balance of water, at pH 5.2-5.4. The aforementioned components are mixed uniformly and then subject to high temperature sterilization for later use.

The rooting and growth-promoting medium contains the following components per liter: 1.2 grams of HYPONEX® No. 1, 1.2 grams of HYPONEX® No. 2, 1 gram of peptone, 20 grams of sucrose, vitamin elements (including myo-inositol) the same as those in MS medium, 0.3 milligrams of NAA, 75 grams of banana juice, 0.75 grams of activated carbon, 6.5 grams of agar, and the balance of water, at pH 5.2-5.4. The aforementioned components are mixed uniformly and then are subject to high temperature sterilization for later use.

The protocorm induction and subculture/proliferation medium contains the following components per liter: 1.5 grams of HYPONEX® No. 1, 1.2 grams of HYPONEX® No. 2, 1 gram of peptone, 75 milliliters of coconut milk, 25 grams of sucrose, vitamin elements (including myo-inositol) the same as those in MS medium, 1.0 milligrams of 6-BA, 6.5 grams of agar, and the balance of water, with the pH of 5.2-5.4. The aforementioned components are mixed uniformly and then subject to high temperature sterilization for later use.

The culture conditions in each of the aforementioned seed germination medium, the in vitro flowering induction medium, the rooting and growth-promoting medium, and the protocorm induction and subculture/proliferation medium are: temperature of 24-28° C., illuminance of 1500-2000 1×, and an illumination period of 14 hours per day.

Embodiment 3: Crossbreeding of *Dendrobium* Red Star and *Dendrobium* Pink Lady

1. Materials: pollination is artificially conducted on selected healthily-growing stock plants of *D.* Red Star and *D.* Pink Lady during the flowering period: and 150 days after the pollination, when the fruits of the two *Dendrobium* varieties have substantially matured, the seeds contained in the respective fruits are aseptically sown.

2. Aseptic sowing: during sowing, the fruits are first soaked in 75% ethanol for 30 seconds, then sterilized in 0.1% mercuric chloride solution for 20 minutes, and rinsed 5 times with sterilized water, and then the fruits are cut open, and the yellowish-white powder-like embryo contained in the fruits is inoculated onto seed germination medium with an inoculating needle and developed under the following culture conditions: temperature of 24-28° C., illuminance of 1500-2000 1×, and an illumination period of 16 hours per day. The seed begins to germinate in about 15 days and thus forms as protocorm, and a complete plantlet is formed in 90 days.

3. In vitro flowering induction and in vitro crossbreeding: the complete plantlets with a height of 2-3 centimeters are transferred onto in vitro flowering induction medium and cultured under the following conditions: temperature of 24-28° C., illuminance of 1500-2000 1×, and an illumination period of 16 hours per day, with 60 days later the flowering rate of *D.* Red Star being 35% and the flowering rate of *D.* Pink Lady being 20%. Interspecific pollination is performed artificially on a super-clean bench between selected in vitro flowers of *D.* Red Star and *D.* Pink Lady having normal flower colors and shapes. After pollination, the flowering plants are transferred onto a rooting and growth-promoting medium and cultured under the following conditions: temperature of 24-28° C., illuminance of 1500-2000 1×, and an illumination period of 16 hours per day. The fruits are matured in just 60 days.

4. Combination of aseptic sowing and in vitro flowering induction of hybrids: the fruit of the previous step matured in vivo is harvested and then cut open without sterilization. The embryo contained in the fruit is sown onto seed germination medium and cultured under the following culture conditions: temperature of 24-28° C., illuminance of 1500-2000 1×, and an illumination period of 16 hours per day. The seed of the hybridized combination germinates to form a protocorm in about 15 days, and a complete plantlet is formed in 80 days. Then the plantlet is transferred onto in vitro flowering induction medium and cultured under the following culture conditions: temperature of 24-28° C., illuminance of 1500-2000 1×, and an illumination period of 16 hours per day, for flowering induction. This allows the flower shapes and colors of the hybridized combination to be observed after the in vivo plantlet blooms.

5. Tissue culture of new varieties: since both of the crossing parents are hybrids, the characters of the progenies are varied significantly. After the plantlet blooms, tissue culture is conducted on selected lines having excellent flower shapes and colors. The stem apex or stem node of a healthily-growing and flowering line selected as the explant is cultured on protocorm induction and subculture/proliferation medium under the following culture conditions: temperature of 24-28° C., illuminance of 1500-2000 1×, and an illumination period of 16 hours per day, for subculture/proliferation. After 40 days, the proliferation times can be 4 (which means the amount is 4 times as the original), and the formed PLB can further proliferate. The PLB may also be transferred onto rooting and growth-promoting medium under the following culture conditions: temperature of 24-28° C., illuminance of 1500-2000 1×, and an illumination period of 16 hours per day, for rooting and promoting growth, so as to obtain in vitro plantlets.

6. Transplanting of in vitro plantlets: The transplanting of in vitro plantlets is conducted when the in vitro plantlets have grown to 3-4 centimeters in height and having 2-3 shoots in each clump. The in vitro plantlets are transplanted to harden them under natural light for 10 days; they are then removed from glass vessels, separating agarized medium from roots by washing, and then the cultivating hardened plantlets in a mixed substrate containing peat and special stones for orchid cultivation (at a 1:1 volumetric ratio), and cultured under conditions that proper ventilation and sufficient moisture are maintained, so as to obtain *Dendrobium* hybrid seedlings, with the transplant survival rate greater than 98%.

The seed germination medium contains the following components per liter: 3 grams of HYPONEX® No. 1, 2 grams of peptone, 100 milliliters of coconut milk, 30 grams of sucrose, vitamin elements (including myo-inositol) the same as those in MS medium, 1 gram of activated carbon, 6.5 grams of agar, and the balance of water, at pH 5.2-5.4. The aforementioned components are mixed uniformly and then subject to high temperature sterilization for later use.

The in vitro flowering induction medium contains the following components per liter: 1.5 grams of HYPONEX® No. 1, 1.5 grams of HYPONEX® No. 2, 0.3 grams of casein hydrolysate, 3.0 milligrams of BA, 0.5 milligrams of NAA, 0.5 milligrams of paclobutrazol, 40 grams of sucrose, vitamin elements (including myo-inositol) the same as those in MS medium, 6.5 grams of agar, and the balance of water, at pH 5.2-5.4. The aforementioned components are mixed uniformly and then subject to high temperature sterilization for later use.

The rooting and growth-promoting medium contains the following components per liter: 2 grams of HYPONEX® No. 1, 1.5 grams of HYPONEX® No. 2, 2 grams of peptone, 30 grams of sucrose, vitamin elements (including myo-inositol) the same as those in MS medium, 0.5 milligrams of NAA, 100 grams of banana juice, 1 gram of activated carbon, 6.5 grams of agar, and the balance of water, at pH 5.2-5.4. The aforementioned components are mixed uniformly and then are subject to high temperature sterilization for later use.

The protocorm induction and subculture/proliferation medium contains the following components per liter: 2 grams of HYPONEX® No. 1, 1.5 grams of HYPONEX® No. 2, 2 grams of peptone, 100 milliliters of coconut milk, 30 grams of sucrose, vitamin elements (including myo-inositol) the same as those in MS medium, 2.0 milligrams of BA, 6.5 grams of agar, and the balance of water, at pH 5.2-5.4. The aforementioned components are mixed uniformly and then subject to high temperature sterilization for later use.

The culture conditions in each of the aforementioned seed germination medium, the in vitro flowering induction medium, the rooting and growth-promoting medium, and the protocorm induction and subculture/proliferation medium are: temperature of 24-28° C., illuminance of 1500-2000 1x, and an illumination period of 16 hours per day.

The invention claimed is:

1. A *Dendrobium* in vitro crossbreeding method, the method comprising the following steps:
   a. aseptically sowing a plurality of seeds obtained from a first plurality of matured fruit of *Dendrobium* stock plants of different varieties that have been artificially pollinated comprising, rinsing the first plurality of matured fruit several times with sterilized water then cutting the first plurality of matured fruit open inoculating a yellowish-white powder-like embryo contained in the first plurality of matured fruit onto a first seed germination medium with an inoculating needle and developing under culture conditions comprising a temperature of 24-28° C., illuminance of 1500-2000 1x, and an illumination period of 12-16 hours per day, allowing germination and forming a plurality of first plantlets with a height of 2-3 centimeters;
   b. in vitro flowering induction and in vitro crossbreeding comprising transferring the plurality of first plantlets with a height of 2-3 centimeters onto a first in vitro flowering induction medium and culturing the plurality of first plantlets under conditions comprising a temperature of 24-28° C., illuminance of 1500-2000 1x, and an illumination period of 12-16 hours per day to obtain a plurality of flowering plants, performing artificial interspecific pollination under aseptic conditions between the plurality of flowering plants of different varieties wherein after pollination the plurality of flowering plants are transferred to a first rooting and growth-promoting medium and cultured under conditions comprising a temperature of 24-28° C., illuminance of 1500-2000 1x, and an illumination period of 12-16 hours per day, to obtain a second plurality of matured fruit;
   c. aseptically sowing and in vitro flowering induction of hybrids comprising cutting open the second plurality of matured fruit, and sowing an embryo contained in the second plurality of matured fruit onto a second seed germination medium and culturing under conditions comprising a temperature of 24-28° C., illuminance of 1500-2000 1x, and an illumination period of 12-16 hours per day allowing germination and forming a second plantlet, and then transferring the second plantlet onto a second in vitro flowering induction medium and culturing under conditions comprising a temperature of 24-28° C., illuminance of 1500-2000 1x, and an illumination period of 12-16 hours per day for flowering induction;
   d. tissue culturing of new varieties comprising selecting a stem apex or stem node of a desired line obtained in step c and culturing on a protocorm induction and subculture/proliferation medium to induce protocorms and subculture proliferation culture conditions comprising a temperature of 24-28° C., illuminance of 1500-2000 1x, and an illumination period of 12-16 hours per day, allowing protocorm-like bodies to form, and then transferring the protocorm-like bodies onto a second rooting and growth-promoting medium and culturing under conditions comprising a temperature of 24-28° C., illuminance of 1500-2000 1x, and an illumination period of 12-16 hours per day, to obtain in vitro plantlets; and
   e. transplanting the in vitro plantlets that have grown to 3-4 centimeters in height for hardening under natural light and then transplanting the hardened plantlets onto a substrate and culturing to obtain *Dendrobium* hybrid seedlings,
   wherein the first and the second seed germination medium contains per liter: 2-3 grams of fertilizer No. 1; 0.5-2 grams of peptone; 50-100 milliliters of coconut milk; 15-30 grams of sucrose; vitamin elements which are the same as those in a Murashige and Skoog (MS) medium, including myo-inositol; 0.5-1 grams of activated carbon; 6~8% of agar; and water, the first and the second seed germination medium having a pH between 5.2-5.4,
   wherein the first and the second in vitro flowering induction medium contains per liter: 1-1.5 grams of fertilizer No. 1; 1-1.5 grams of fertilizer No. 2; 0.1-0.3 grams of casein hydrolysate; 0.5-3.0 milligrams of 6-benzyladenine; 0.1-0.5 milligrams of naphthylacetic acid; 0.1-0.5 milligrams of paclobutrazol; 30-40 grams of sucrose; vitamin elements which are the same as those in the MS medium, including myo-inositol; 6-8% of agar; and water, the first and the second in vitro flowering induction medium having a pH between 5.2-5.4, wherein the first and the second rooting and growth-promoting medium contains per liter: 1-2 grams of fertilizer No. 1; 1-1.5 grams of fertilizer No. 2; 0.5-2 grams of peptone; 15-30 grams of sucrose; vitamin elements which are the same as those in the MS medium, including myo-inositol; 0.1-0.5 milligrams of naphthylacetic acid; 50-100 grams of banana juice; 0.5-1 gram of activated carbon; 6-8% of agar; and water, the first and the second rooting and growth-promoting medium having a pH between 5.2-5.4, wherein the protocorm induction and subculture/proliferation medium contains per liter: 1-2 grams of fertilizer No. 1; 1-1.5 grams of fertilizer No. 2; 0.5-2 grams of peptone; 50-100 milliliters of coconut milk; 20-30 grams of sucrose; vitamin elements which are the same as those in the MS medium, including myo-inositol; 0.5-2.0 milligrams of 6-benzyladenine; 6~8% of agar; and water, the protocorm induction and subculture/proliferation medium having a pH between 5.2-5.4, wherein the fertilizer No. 1 contains 7 wt % of total nitrogen, 6 wt % of water-soluble phosphoric anhydride and 19 wt % of water-soluble potassium oxide, the 7 wt % of total nitrogen including 1.2% of ammonium nitrogen and 5.8% of nitrate nitrogen; the fertilizer No. 2 contains 20 wt % of total nitrogen, 20 wt % of water-soluble phosphoric anhydride and 20 wt % of water-soluble potassium oxide, the 20 wt % of total nitrogen including 4% of ammonium nitrogen and 4% of nitrate nitrogen.

2. The *Dendrobium* in vitro crossbreeding method of claim 1, wherein step a includes, at first, soaking the first plurality of matured fruit in 75% ethanol for 30 seconds, then sterilizing the first plurality of matured fruit in 0.1% mercuric chloride solution for 20 minutes, and then rinsing the first plurality of matured fruit with sterilized water 4-5 times.

3. The *Dendrobium* in vitro crossbreeding method of claim 1, wherein the protocorm-like bodies of step d are re-inoculated conditions comprising culturing at a temperature of 24-28° C., illuminance of 1500-2000 1x, and an illumination period of 12-16 hours per day, before being transferred onto the second rooting and growth-promoting medium.

4. The *Dendrobium* in vitro crossbreeding method of claim 1, wherein the transplanting of in vitro plantlets in step e is conducted when the in vitro plantlet have grown to a height of 3-4 centimeters and with 2-3 shoots comprising hardening the in vitro plantlets under natural light for 10 days to obtain hardened plantlets; washing the roots of the hardened plantlets cultivating the hardened plantlets in a mixed substrate containing peat and stones for orchid cultivation at a 1:1 volumetric ratio, and then culturing the hardened plantlets under natural conditions to obtain *Dendrobium* hybrid seedlings.

* * * * *